United States Patent [19]

Manura et al.

[11] Patent Number: 5,596,876
[45] Date of Patent: Jan. 28, 1997

[54] MINIATURIZED CRYOGENIC TRAP APPARATUS

[75] Inventors: John J. Manura, Pennington, N.J.; Christopher W. Baker, Doylestown, Pa.; John N. Manos, Mercerville, N.J.

[73] Assignee: Scientific Instrument Services, Inc., Ringoes, N.J.

[21] Appl. No.: 566,577

[22] Filed: Nov. 28, 1995

[51] Int. Cl.⁶ .......................... B01D 8/00; B01D 15/08
[52] U.S. Cl. .................................. 62/55.5; 95/87
[58] Field of Search ................ 62/55.5, 600; 55/268, 55/267, DIG. 15; 95/87

[56] References Cited

U.S. PATENT DOCUMENTS

| | | |
|---|---|---|
| 3,695,003 | 10/1972 | Bednarski . |
| 4,124,358 | 11/1978 | Muller . |
| 4,213,326 | 7/1980 | Brodasky . |
| 4,245,494 | 1/1981 | Legendre et al. . |
| 4,305,275 | 12/1981 | Firth . |
| 4,432,225 | 2/1984 | Hayes et al. . |
| 4,479,380 | 10/1984 | Novotny et al. . |
| 4,668,091 | 5/1987 | Lagesson et al. . |
| 4,672,042 | 6/1987 | Ross, Jr. et al. . |
| 4,766,760 | 8/1988 | Poshemansky et al. . |
| 4,863,871 | 9/1989 | Munari et al. . |
| 4,923,486 | 5/1990 | Rubey . |
| 4,944,781 | 7/1990 | Ruggirello et al. . |
| 4,948,389 | 8/1990 | Klein et al. . |
| 4,991,423 | 2/1991 | Poshemansky et al. . |
| 5,048,322 | 9/1991 | Hiller et al. . |
| 5,065,614 | 11/1991 | Hartman et al. . |
| 5,083,450 | 1/1992 | Grindstaff . |
| 5,094,099 | 3/1992 | Ross . |
| 5,096,471 | 3/1992 | Sacks et al. . |
| 5,141,534 | 8/1992 | Sacks et al. . |
| 5,227,059 | 7/1993 | Shepherd . |
| 5,228,514 | 7/1993 | Worden et al. . |
| 5,236,668 | 8/1993 | Higdon . |
| 5,242,471 | 9/1993 | Markham et al. ................. 95/87 |
| 5,252,109 | 10/1993 | Munari et al. . |
| 5,345,787 | 9/1994 | Piltingsrud ................... 62/55.5 |
| 5,391,221 | 2/1995 | Fukushima et al. . |
| 5,402,668 | 4/1995 | Murakami et al. ............. 73/19.02 |
| 5,447,556 | 9/1995 | Pleil et al. ...................... 95/87 |

Primary Examiner—William Doerrler
Attorney, Agent, or Firm—Sperry, Zoda & Kane

[57] ABSTRACT

A cryogenic trap apparatus for cooling is disclosed as well as heating of a capillary column in order to analyze the volatile components of any volatile or semi-volatile compound passing through the capillary column. The cryogenic trap is restricted to treatment of one inch or less in length of the capillary column in order to achieve miniaturization of the design. A cylindrically shaped main cryogenic chamber with a volume of less than 0.5 cubic inches is adapted to receive the capillary column extending axially therethrough and includes a cooling fluid inlet and a cooling fluid outlet as well as a heating apparatus for achieving rapid cooling and thereafter rapid heating of the components in the capillary column for trapping and segregating individual components thereof for chromatographic analysis.

20 Claims, 4 Drawing Sheets

MINIATURIZED CRYOGENIC TRAP APPARATUS

BACKGROUND OF THE INVENTION

1. Field of the Invention

The present invention deals with the field of devices for cryogenically trapping gaseous fractions of fluid mixtures. Such mixtures normally move through capillary tubes which are cooled by the cryogenic trap to facilitate separation of components of the sample. Heating means is also included for rapidly vaporizing the solidified or liquified gas component for chromatographic analysis thereof.

2. Description of the Prior Art

Numerous devices have been designed for such chromatographic analysis such as shown in U.S. Pat. No. 3,695,003 patented Oct. 3, 1972 to V. Bednarski on a "Gas Chromatography Method And Apparatus"; and U.S. Pat. No. 4,124,358 patented Nov. 7, 1978 to F. Muller and assigned to Siemens Aktiengesellschaft on a "Sample-Injection Device For Process Gas Chromatography With Capillary Columns"; and U.S. Pat. No. 4,213,326 patented Jul. 22, 1980 to T. Brodasky and assigned to The Upjohn Company on a "Sample Supply Device"; and U.S. Pat. No. 4,245,494 patented Jan. 20, 1981 to M. Legendre et al and assigned to The United States of America as represented by the Secretary of Agriculture on an "Inlet System For Direct Gas Chromatographic And Combined Gas Chromatographic/ Mass Spectrometric Analysis Of Food Volatiles"; and U.S. Pat. No. 4,305,275 patented Dec. 15, 1981 to F. Fifth and assigned to Applied Plastics Co., Inc. on a "Chromatographic Apparatus And Method Of Operation"; and U.S. Pat. No. 4,432,225 patented Feb. 21, 1984 to J. Hayes et al and assigned to The United States of America as represented by the United States Department of Energy on a "Detection System For A Gas Chromatograph"; and U.S. Pat. No. 4,479,380 patented Oct. 30, 1984 to M. Novotny et al and assigned to Brigham Young University on an "Open-Tubular Supercritical Fluid Chromatography"; and U.S. Pat. No. 4,668,091 patented May 26, 1987 to V. Lagesson et al on an "Arrangement At A Gas Flow Through Cell For Spectrophotometric Analysis Of Chemical Compounds"; and U.S. Pat. No. 4,672,042 patented Jun. 9, 1987 to J. Ross, Jr. et al and assigned to Orion Research Puerto Rico, Inc. on a "Method Of And Apparatus For Chromatographic Analysis"; and U.S. Pat. No. 4,766,760 patented Aug. 30, 1988 to V. Poshemansky et al and assigned to Vsesojuzny Nauchno-issledovatelsky i Konstruktorsky istitute on a "Method For Chromatographic Analysis Of A Mixture Of Liquid Substances And A Gas Chromatograph For Carrying Out The Method"; and U.S. Pat. No. 4,863,871 patented Sep. 5, 1989 to F. Munari et al and assigned to Carlo Erba Strumentazione S.p.A. on a "Method And Device For Adjusting The Cooling Temperature Of A Sample Trap In An Apparatus For Gas Chromatographic Analysis"; and U.S. Pat. No. 4,923,486 patented May 8, 1990 to W. Rubey and assigned to University of Dayton on a "Gas Chromatography Methods And Apparatus"; and U.S. Pat. No. 4,944,781 patented Jul. 31, 1990 to D. Ruggirello et al and assigned to Schering Corporation on a "Gas Chromatograph/Autosampler Coupling Assembly"; and U.S. Pat. No. 4,948,389 patented Aug. 14, 1990 to K. Klein et al and assigned to Hewlett-Packard Company on a "Gas Chromatograph Having Cryo Blast Coolings"; and U.S. Pat. No. 4,991,423 patented Feb. 12, 1991 to V. Poshemansky et al on a "Method Of Gas-Chromatographic Analysis Of Mixtures And Device Therefor"; and U.S. Pat. No. 5,048,322 patented Sep. 17, 1991 to J. Hiller et al and assigned to The Dow Chemical Company on a "Heated Column Inlet Gas Chromatography Method And Apparatus"; and U.S. Pat. No. 5,065,614 patented Nov. 19, 1991 to T. Hartman et al and assigned to Rutgers University on a "Short Path Thermal Desorption Apparatus For Use In Gas Chromatography Techniques"; and U.S. Pat. No. 5,083,450 patented Jan. 28, 1992 to Q. Grindstaff and assigned to Martin Marietta Energy Systems, Inc. on a "Gas Chromatograph-Mass Spectrometer (GC/MS) System For Quantitative Analysis Of Reactive Chemical Compounds"; and U.S. Pat. No. 5,094,099 patented Mar. 10, 1992 to R. Ross on a "Chromatographic Collection Apparatus And Method For Sequential Condensed And Vapor Phase Spectroscopic Studies"; and U.S. Pat. No. 5,096,471 patented Mar. 17, 1992 to R. Sacks et al and assigned to The Regents Of The University of Michigan on a "Gas Chromatography System And Methods"; and U.S. Pat. No. 5,141,534 patented Aug. 25, 1992 to R. Sacks et al and assigned to The Regents Of The University of Michigan on a "Sample Collection And Inlet Systems For Gas Chromatography Apparatus"; and U.S. Pat. No. 5,227,059 patented Jul. 13, 1993 to P. Shepherd and assigned to Alltech Associates, Inc. on "Chromatography Columns"; and U.S. Pat. No. 5,228,514 patented Jul. 20, 1993 to R. Worden et al and assigned to Ruska Laboratories, Inc. on a "Gas Trap Apparatus"; and U.S. Pat. No. 5,236,668 patented Aug. 17, 1993 to W. Higdon on a "Detachable Column Cartridge Gas Chromatograph"; and U.S. Pat. No. 5,252,109 patented Oct. 12, 1993 to F. Munari et al and assigned to Carlo Erba Strumentazione S.p.A. on a "Gas Chromatographic Injector"; and U.S. Pat. No. 5,391,221 patented Feb. 21, 1995 to T. Fukushima et al and assigned to Shimadzu Corporation on a "Gas Chromatograph And Method Of Using Same".

SUMMARY OF THE INVENTION

The present invention provides a cryogenic trap apparatus which is miniaturized. This miniaturization is made possible by treatment of only one inch or less of the capillary column length by the cryogenic trap which has many unique advantages such as conservation of energy required for such high speed cooling as well as heating thereof. Also the miniaturization of the main chamber of the cryogenic trap significantly minimizes problems associated with leakage therefrom.

The miniaturized cryogenic trap preferably is usable along with a gas chromatography oven and a conventional gas chromatography injection port member which is normally positioned extending into the oven and is adapted to guide a capillary column thereinto for analysis. Cryogenic traps of the prior art are often secured to the inside surface of the top, bottom or side walls of the oven. The present apparatus provides a unique configuration wherein the cryogenic trap apparatus now miniaturized is capable of being secured directly to the injection port member by a bracket means.

The configuration of the miniaturized cryogenic trap member includes a main housing which preferably defines a main chamber therein for selectively cooling and heating. The main chamber is preferably of a generally cylindrical shape wherein the diameter of the base of the cylinder is less than 0.75 inches and the height of the cylindrical shape of the main chamber is less than one inch. With the capillary column heating axially through the cylindrically shaped main chamber this will allow the main chamber to treat one inch or less in total length of the capillary column itself and will minimize the total volume of the main chamber to less than 0.5 cubic inches.

Preferably also the main housing will define an upper opening therein with an upper shoulder means extending peripherally around the opening. A capillary guide tube will preferably be included of stainless steel material which extends into the main housing axially through the cylindrically shaped main chamber such as to expose one inch or less thereof to the main chamber of the cryogenic trap. This capillary guide tube will preferably be fixedly attached to the main housing in such a manner as to minimize leakage from the main chamber defined therein. This capillary guide tube will define a feedthrough bore extending longitudinally therethrough which is adapted to receive the capillary column preferably of fused silica extending therethrough for selectively heating and cooling of volatile components passing therethrough responsive to selective cooling and heating of the main chamber. This feedthrough bore will extend through the main chamber along the distance of not greater than one inch in length in order to achieve miniaturization of the cryogenic trap and of the main chamber thereof.

The above described port bracket member is preferably fixedly secured to the main housing and is detachably mountable to the injection port member to facilitate positioning of the capillary column within the feedthrough bore of the capillary guide tube after exiting thereof from the injection port member. An insulation member will also preferably be positioned between the port bracket member and the injection port member in order to minimize heat flow therebetween and maintain the thermal integrity of the injection port and the cryogenic trap.

A cooling fluid inlet will preferably be defined in the housing in fluid flow communication with respect to the main chamber for selectively supplying cooling fluid therein for cooling of the feedthrough bore extending therethrough and for cooling of the volatile components passing through the capillary column positioned extending therethrough. This cooling fluid can be any chosen liquid or gas capable of achieving such cooling. However, with most systems the cooling fluid used is liquid carbon dioxide or liquid nitrogen, or, in some applications, air can be used. Carbon dioxide has been found useful to cooling to as low as −70 degrees Centigrade whereas liquid nitrogen permits cooling below that level to a level as low as −180 degrees Centigrade.

In a similar manner a cooling fluid outlet can be defined in the housing in fluid flow communication with respect to the main chamber for selectively exhausting cooling fluid therefrom in order to allow subsequent heating of the feedthrough bore extending therethrough and for allowing heating of the volatile components passing through the capillary column positioned extending therethrough.

The design of the present invention further includes an upper plate positioned in abutment with the upper shoulder peripherally around the upper opening defined in the main housing. This upper plate is designed to extend over the upper opening for sealing thereof and preventing fluid flow leakage from the main chamber outwardly therepast. The upper plate member is designed to be in abutment with the upper shoulder in order to facilitate sealing. The upper plate further defines a plurality of upper plate apertures therein to facilitate access therebelow into the main chamber. A cap member is designed to be positioned attached to the main housing in a position extending over the upper plate and extending outwardly therefrom to define an upper chamber thereabove. The cap means further defines a laterally opening therein to facilitate access thereinto.

A heating device is at least partially positioned within the main chamber extending about the feedthrough bore to facilitate heating of the capillary column and of the volatile components passing therethrough. This heating device preferably includes an electrical resistance heating element extending about the capillary tube within the main chamber to facilitate selective heating of the capillary column extending therethrough. This heating means further includes electrical lines extending through the lateral opening of the cap into the upper chamber defined therein and through the upper plate apertures into the main chamber for operative electrical connection with respect to the electrical resistance heating element positioned encircling the capillary guide tube.

A temperature controlling device is included having a temperature probe positioned within the main chamber and a temperature monitoring line extending outwardly from the probe. This temperature controlling means includes a heating means for controlling operation thereof responsive to temperatures monitored within the main chamber by the temperature probe. This temperature monitoring line extends through the lateral opening and through one of the upper plate apertures into the main chamber for operative connection with respect to the temperature probe.

In order to facilitate sealing of the main chamber a plurality of annular sealing collars with holes extending vertically therethrough are positioned with one each in each of the upper plate apertures for abutting engagement with respect to the electrical lines as well as with respect to the temperature monitoring line passing through the upper plate. In this manner the annular sealing collars will surround and abut both the electrical lines and the temperature monitoring line as they pass through the holes in the collars to allow them to pass from the upper chamber to the main chamber while minimizing fluid flow leakage from the main chamber. These annular sealing collars and, particularly, the holes therein are preferably capable of being sized as needed to define various sized diameters depending upon the size of the temperature monitoring line and the electrical lines of the heating device.

In the preferred design of the present invention an auxiliary lateral housing means is also included attached to the main housing and adapted to receive the temperature controlling means fixedly secured thereto. This lateral housing can include a thermal transition joint as well as a thermocouple junction included in the temperature sensing means. The temperature controlling means preferably can include a thermocouple junction means and can be a platinum resistance thermometer for accurately and quickly controlling temperatures in the miniaturized cryogenic trap apparatus of the present invention. In the present invention it is preferred that the heating means is selectively operable to a capacity such that it will be capable of increasing the temperature of the volatile components passing through the capillary column with a heat increasing or ramp speed of 1200 degrees Centigrade per minute.

It is an object of the present invention to provide a miniaturized cryogenic trap apparatus for selectively cooling and heating of a capillary column for analyzing of volatile components passing therethrough wherein liquid nitrogen used for cooling is substantially conserved.

It is an object of the present invention to provide a miniaturized cryogenic trap apparatus for selectively cooling and heating of a capillary column for analyzing of volatile components passing therethrough wherein liquid carbon dioxide used for cooling is substantially conserved.

It is an object of the present invention to provide a miniaturized cryogenic trap apparatus for selectively cooling and heating of a capillary column for analyzing of volatile components passing therethrough wherein electric current utilized for resistance heating is substantially conserved.

It is an object of the present invention to provide a miniaturized cryogenic trap apparatus for selectively cooling and heating of a capillary column for analyzing of volatile components passing therethrough wherein fluid flow leakage from the main cryogenic chamber is minimized.

It is an object of the present invention to provide a miniaturized cryogenic trap apparatus for selectively cooling and heating of a capillary column for analyzing of volatile components passing therethrough which is mounted directly with respect to a gas chromatography injection port member by an insulated mounting bracket.

It is an object of the present invention to provide a miniaturized cryogenic trap apparatus for selectively cooling and heating of a capillary column for analyzing of volatile components passing therethrough wherein the capillary column does not pass through any metal fittings whatsoever such that there is no exposure of any of the organic analytes to any metallic surfaces.

It is an object of the present invention to provide a miniaturized cryogenic trap apparatus for selectively cooling and heating of a capillary column for analyzing of volatile components passing therethrough wherein a thermocouple junction can be included within the temperature sensing means.

It is an object of the present invention to provide a miniaturized cryogenic trap apparatus for selectively cooling and heating of a capillary column for analyzing of volatile components passing therethrough wherein a platinum resistance thermometer can be included to control heating within the cryogenic chamber.

It is an object of the present invention to provide a miniaturized cryogenic trap apparatus for selectively cooling and heating of a capillary column for analyzing of volatile components passing therethrough wherein liquid carbon dioxide can be used for cooling of the cryogenic chamber without any icing resulting therefrom.

It is an object of the present invention to provide a miniaturized cryogenic trap apparatus for selectively cooling and heating of a capillary column for analyzing of volatile components passing therethrough wherein the analytes appear in narrower bands with higher sensitivity.

It is an object of the present invention to provide a miniaturized cryogenic trap apparatus for selectively cooling and heating of a capillary column for analyzing of volatile components passing therethrough wherein the chromatographic output has greater sensitivity.

It is an object of the present invention to provide a miniaturized cryogenic trap apparatus for selectively cooling and heating of a capillary column for analyzing of volatile components passing therethrough wherein a fused silica capillary column is fed through a stainless steel capillary guide tube with snug frictional engagement therebetween to facilitate retainment therein and chromatographic analysis.

It is an object of the present invention to provide a miniaturized cryogenic trap apparatus for selectively cooling and heating of a capillary column for analyzing of volatile components passing therethrough wherein heating of the capillary column can be achieved at a ramp speed of as great as 1200 degrees Centigrade per minute.

It is an object of the present invention to provide a miniaturized cryogenic trap apparatus for selectively cooling and heating of a capillary column for analyzing of volatile components passing therethrough wherein the cryogenic trap can be positioned inside of the gas chromatography oven at any location including adjacent the gas chromatography injection port area rather than being required to be mounted upon the bottom of the oven itself or at any specific location therein.

It is an object of the present invention to provide a miniaturized cryogenic trap apparatus for selectively cooling and heating of a capillary column for analyzing of volatile components passing therethrough wherein trapping of the gas chromatography volatile components can be achieved at the front end of the capillary column.

It is an object of the present invention to provide a miniaturized cryogenic trap apparatus for selectively cooling and heating of a capillary column for analyzing of volatile components passing therethrough wherein the miniaturized cryogenic trap can be positioned adjacent to the injection port member to facilitate gas injection techniques such as headspace injection, thermal desorption and other gas and liquid injection methods.

It is an object of the present invention to provide a miniaturized cryogenic trap apparatus for selectively cooling and heating of a capillary column for analyzing of volatile components passing therethrough wherein the cooling temperature can be maintained to an accuracy of within five degrees of the desired temperature.

It is an object of the present invention to provide a miniaturized cryogenic trap apparatus for selectively cooling and heating of a capillary column for analyzing of volatile components passing therethrough wherein the cryogenic trap can be maintained at a cold temperature for a time period anywhere from one minute to thirty minutes or even longer depending upon the analytic technique being utilized.

It is an object of the present invention to provide a miniaturized cryogenic trap apparatus for selectively cooling and heating of a capillary column for analyzing of volatile components passing therethrough wherein the cryogenic trap apparatus can be rapidly heated with a high thermal ramp speed to release the volatiles in a narrow plug for subsequent chromatography on the capillary column within the chromatography oven.

It is an object of the present invention to provide a miniaturized cryogenic trap apparatus for selectively cooling and heating of a capillary column for analyzing of volatile components passing therethrough wherein physical space within a chromatography oven is conserved by the use of the miniaturized sized cryogenic trap apparatus of the present invention.

It is an object of the present invention to provide a miniaturized cryogenic trap apparatus for selectively cooling and heating of a capillary column for analyzing of volatile components passing therethrough wherein the sample can be trapped at the very front of the capillary column thereby providing an increased resolution of the gas chromatography peaks.

It is an object of the present invention to provide a miniaturized cryogenic trap apparatus for selectively cooling and heating of a capillary column for analyzing of volatile components passing therethrough wherein the miniaturized cryogenic trap can be positioned at any location within a chromatography oven such as would be useful in techniques such as multi-dimensional gas chromatography.

It is an object of the present invention to provide a miniaturized cryogenic trap apparatus for selectively cooling and heating of a capillary column for analyzing of volatile components passing therethrough wherein maximum sensitivity of analysis is provided since no sample is lost due to catalytic reactions with any metal surfaces since the capillary column is exposed to no fittings or metal surfaces whatsoever in that it passes through the capillary column which is preferably formed of fused silica.

It is an object of the present invention to provide a miniaturized cryogenic trap apparatus for selectively cooling and heating of a capillary column for analyzing of volatile components passing therethrough wherein use with head space gas chromatography injections is facilitated.

It is an object of the present invention to provide a miniaturized cryogenic trap apparatus for selectively cooling and heating of a capillary column for analyzing of volatile components passing therethrough wherein use with thermal desorption injection techniques is facilitated.

It is an object of the present invention to provide a miniaturized cryogenic trap apparatus for selectively cooling and heating of a capillary column for analyzing of volatile components passing therethrough wherein use with pyrolysis gas chromatography injection is facilitated.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

DETAILED DESCRIPTION OF THE PREFERRED EMBODIMENT

The present invention is designed to provide a miniaturized cryogenic trap 16 for the purpose of trapping of a fluid sample for chromatographic analysis thereof. The sample is cooled into a liquid or, more preferably, a solid state cryogenically within the trap of the present design and thereafter is heated for vaporizing of the sample to facilitate chromatographic analysis.

Figure 3:
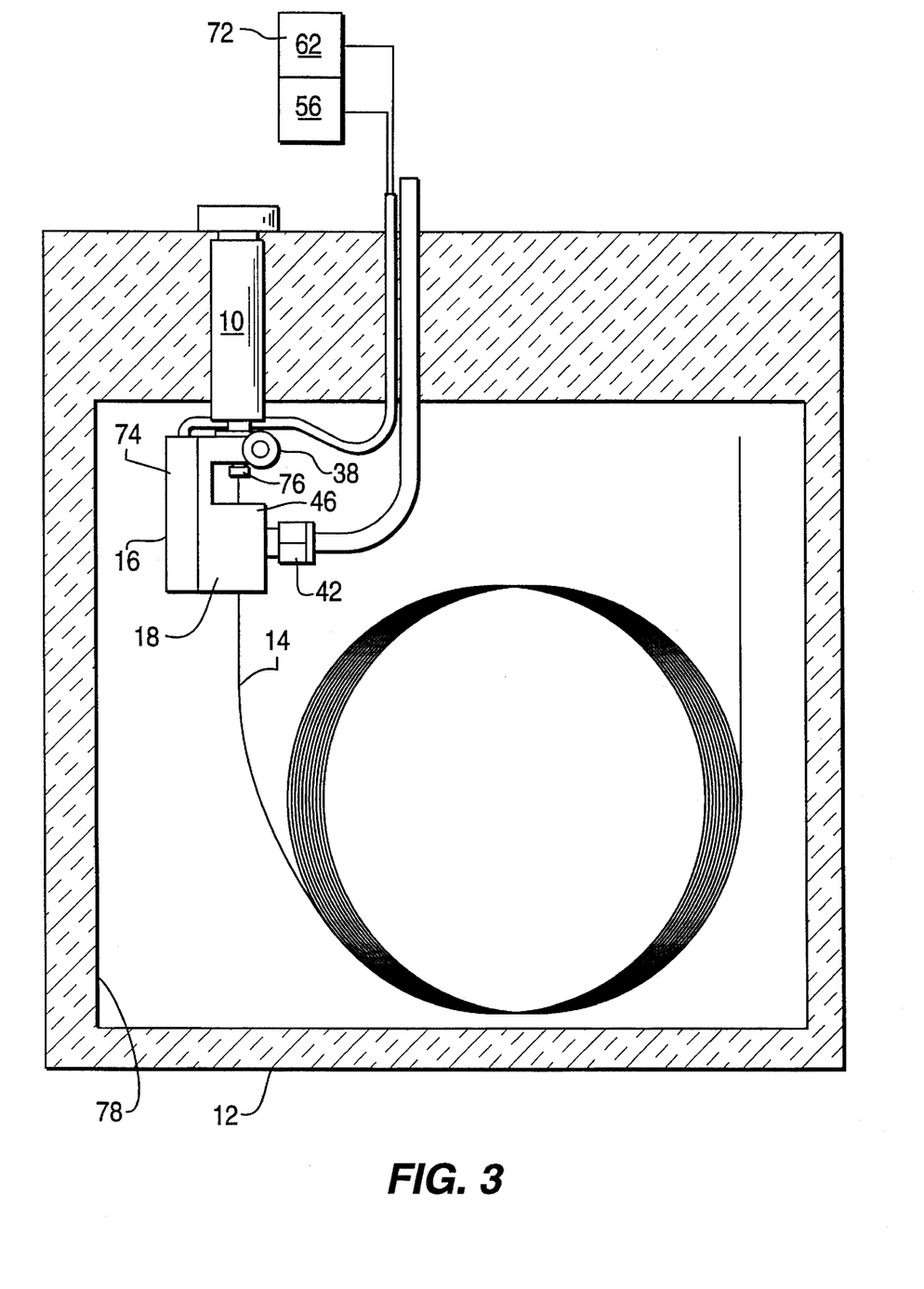
FIG. 3 is an illustration of an embodiment of the apparatus of the present invention shown mounted upon an injection port positioned within a chromatography oven.

In conventional configurations a gas chromatography oven 12 is provided and is adapted to receive a capillary column 14 passing thereinto. The capillary column 14 positioning in the gas chromatography oven 12 is determined by an injection port member 10. Injection port member 10 is preferably positioned in the GC oven wall 78 and includes an injection port insulation liner 80 for minimizing thermal transfer between the capillary column 14 and the wall 78 of the GC oven 12.

Figure 2:
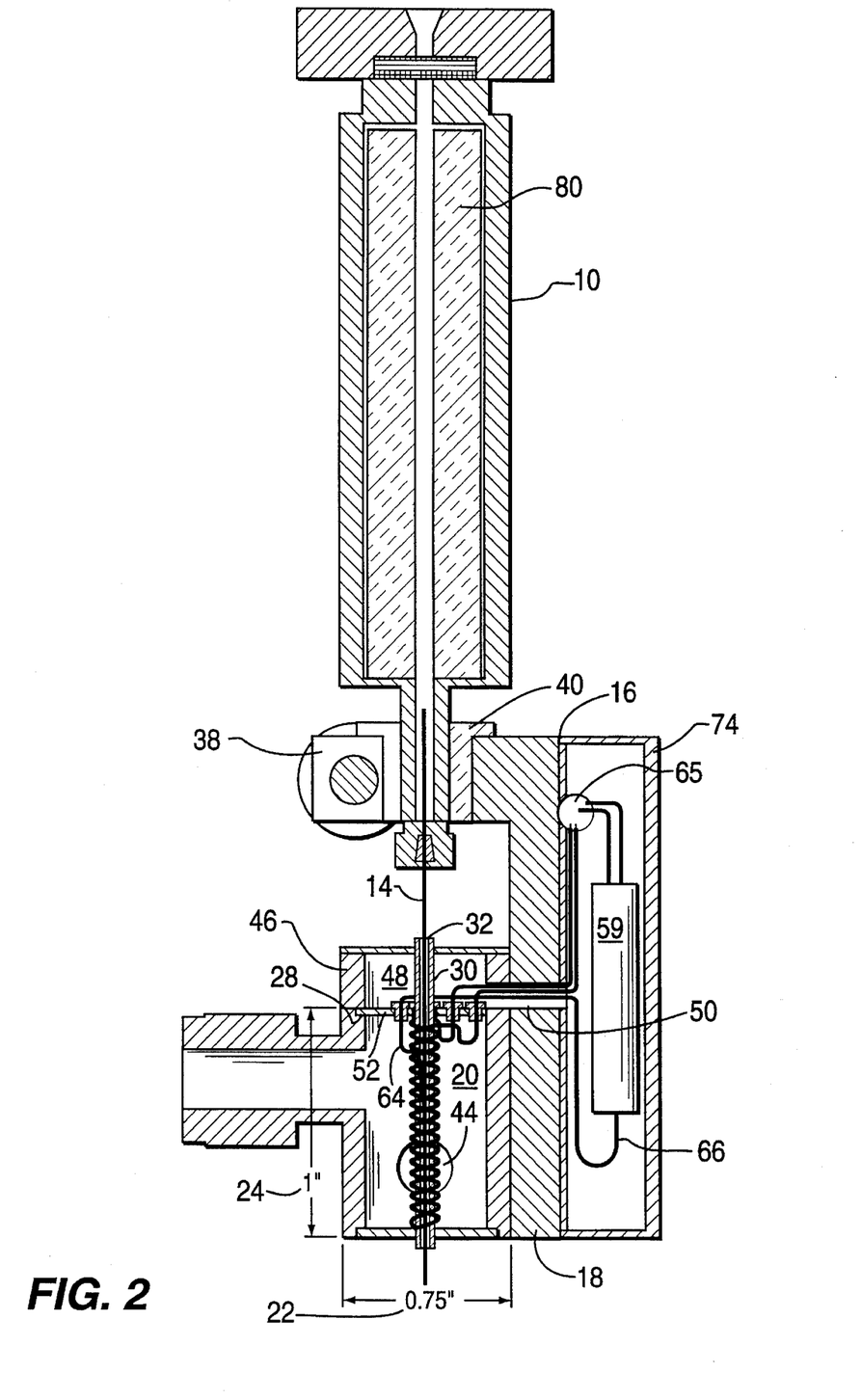
FIG. 2 is a side cross-sectional view of the embodiment shown in FIG. 1.

The miniaturized cryogenic trap apparatus 16 of the present invention includes a main housing 18 which defines a main chamber 20 therein. Main chamber 20 is designed for cryogenic treatment of a capillary column passing therethrough and for heating thereof. The main chamber 20 preferably is of a cylindrical shape with the capillary column 14 passing axially therethrough. The cryogenic trap apparatus of the present invention is miniaturized in that the extent of the length of the capillary column 14 which passes through the cryogenic main chamber 20 is limited to one inch or less in order to facilitate gas chromatographic analysis and for other important advantages including energy conservation and allowing rapid temperature changes to aid in analyte trapping as well as other advantages.

With this miniaturized configuration for the cryogenic trap apparatus 16 the cylindrical main chamber will preferably be formed with a cylindrical base 22 having a diameter of not greater than 0.75 inches and a cylindrical height 24 having a dimension of not greater than one inch. In this manner the total overall volume of the main chamber 20 will be miniaturized to a total volume of not greater than 0.5 cubic inches. This miniaturization achieves many advantages in the gas chromatographic analysis which will be explained below.

The main housing 18 preferably defines an upper opening 26 with an upper shoulder 28 extending peripherally around the opening 26. The upper opening 26 is designed to be closed by positioning of an upper plate 52 thereacross. The upper plate 52 is designed to be positioned in abutment with respect to the upper shoulder 28 for sealing against the main chamber 20 thereby preventing fluid flow leakage from the main chamber 20 within the main housing 18.

A capillary guide tube 30 preferably of a stainless steel material is designed to extend axially through the cylindrically Shaped main housing 18. Capillary guide tube 30 will define a feedthrough bore 32 longitudinally therealong which has a portion extending through the main housing 18 along a length of one inch or less. The capillary column 14 is adapted to extend from the injection port member 10 downwardly through the injection port nut 76 and into the feedthrough bore means 32 of capillary guide tube 30. In this manner the capillary column 14 will avoid contact with any metallic fittings or other surfaces which may adversely affect the chromatographic analysis of volatile and semi-volatile components passing therethrough. Preferably the capillary column 14 will be formed of a fused silica material and be in frictional engagement with respect to the internal diameter of the feedthrough bore means 32 in order to facilitate positioning and retaining therewithin.

Figure 1:
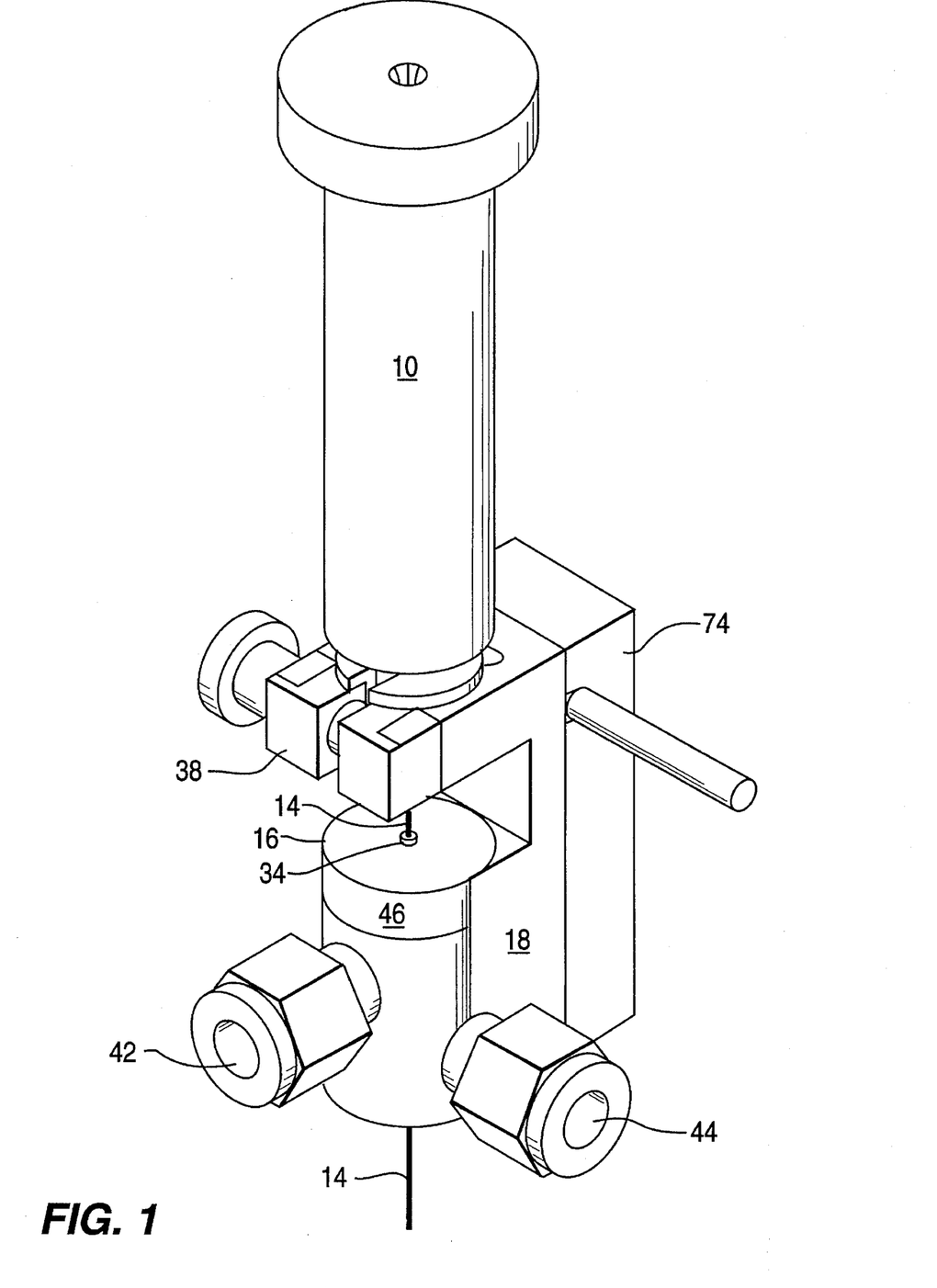
FIG. 1 is a perspective illustration of an embodiment of the miniaturized cryogenic trap apparatus of the present invention shown mounted upon a gas chromatography injection port member.

The miniaturized cryogenic trap apparatus of the present invention preferably includes a port bracket member 38 which is designed to be detachably securable with respect to an injection port member 10. It is also preferable to minimize any thermal flow between the port bracket member 38 and the injection port member 10 and, as such, a thermal insulation member 40 may be positioned therebetween.

Cooling of the main chamber 20 for cryogenic trapping within the capillary column 14 is achieved by a cooling fluid inlet 42 which can be connected to any supply of cooling material such as liquid nitrogen or liquid carbon dioxide, or even air under certain parameters. A cooling fluid outlet 44 may also be defined in the main housing in fluid flow communication with the main chamber 20 to exhaust cooling fluid therefrom after the desired cryogenic trapping has taken place.

To facilitate control of the heating of the capillary column within the cryogenic trap a cap member 46 may be included positioned extending over the upper opening 26 covered by the upper plate 52. This cap 46 along with the main housing 18 and the upper plate 52 will define an upper chamber 48. This upper chamber is designed to receive electrical leads and the thermostat sensing line extending therein to facilitate access thereof into the interior of the main chamber 20 therebelow.

Figure 4:
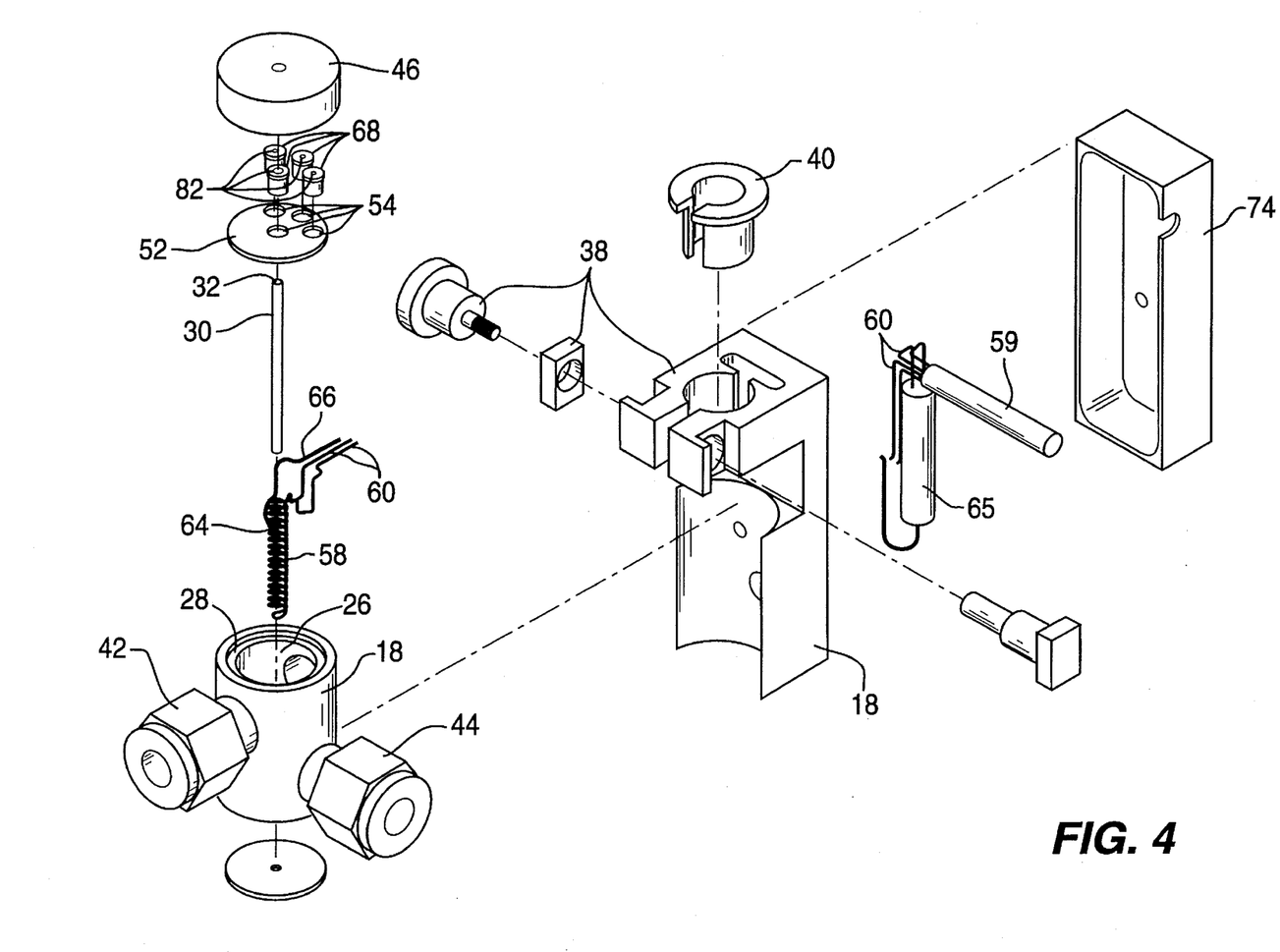
FIG. 4 is an exploded view of the embodiment of the apparatus shown in FIG. 1.

The cap 46 also defines a lateral opening 50 therein to facilitate entry of the electrical lead lines or the probe sensing lines thereinto. Upper plate 52 defines a plurality of upper plate apertures 54 defined therein as best shown in FIGS. 2 and 4. Upper plate apertures 54 are designed to removable receive annular sealing collars 68 therein.

In the configuration of the present invention as shown in this preferred embodiment the heating apparatus 56 includes an electrical resistance heating element 58 which extends peripherally about the capillary guide tube 30 which receives the capillary column 14 extending therethrough. This electrical resistance heating element 58 is connected through electrical lines 60 and a thermal transition joint 65 to a heating means 56 located externally from the main housing 18. In a similar manner a temperature controlling means 62 is defined including a temperature probe 64 is preferably positioned adjacent to the electrical resistance heating element 58 for sensing of the immediate environmental temperature thereof. Temperature probe 64 is connected through a temperature monitoring line 66 to a thermocouple junction 59 and to the remotely position temperature controlling means 62. Temperature controlling means 62 can include a platinum resistance thermometer 72. Preferably the temperature monitoring means and thermocouple junction are both included within an auxiliary lateral housing 74 as shown best in FIG. 2.

In this preferred embodiment it is necessary to provide a means for communicating the electrical line 60 of the heating means 56 as well as the temperature monitoring line 66 of the temperature controlling means 62 from the external environment into the main housing 18 without compromising the seal of the main chamber 20. This is achieved by proper choice in sizing of the removable annular sealing collars 68. As shown best in FIG. 4, these collars can be used to achieve a snug sealing relationship in abutment with the electrical lines 60 and the temperature probe 64 as they pass through the upper plate apertures 54 in the upper plate 52 and through the holes 82 in the collars 68. One of these annular sealing collars 68 can also be used to be positioned in surrounding relationship to the stainless steel capillary guide tube 30 and may indeed be fixedly secured thereto such as by soldering or welding. The annular sealing collars 68 can all define holes extending therethrough which are of a size to preferably closely abut the electrical lines 60 or the temperature monitoring line 66 passing therethrough. In this manner a miniaturized cryogenic trap apparatus can be provided which provides electrical access to the heating element 58 and the temperature probe 64 positioned within the main housing 18 while at the same time maintaining the sealed environment of the main chamber 20.

In use, the miniaturized cryogenic trapping apparatus 16 of the present invention is particularly usable when positioned within the interior of a gas chromatography oven wall 78. With this usage the apparatus 16 of the present invention is particularly useful for the trapping of gas chromatography volatile components at the very front end of a capillary column as it passes into an oven. In most configurations the trap apparatus 16 of the present invention will be mounted directly onto the injection port member 10 of a GC oven 12 by way of the port bracket member 38 in order that the cryogenic trap be positioned surrounding the capillary column 14 immediately upon entry of volatile and semi-volatile components thereof into the oven environment. However, the miniaturized cryogenic trap apparatus 16 of the present invention can also be used in situations where it is not secured to an injection port 10 within a GC oven wall 78 such as when used with general pyrolysis techniques or direct thermal injection of solid or liquid samples. Furthermore the miniaturized cryogenic trap 16 of the present invention can be mounted anywhere within a gas chromatography oven in order to trap volatiles and semi-volatiles after chromatography has begun for use with common techniques often referred to as multi-dimensional chromatography. The cryogenic trap apparatus 16 of the present invention being miniaturized is also more universally usable with different coolants. Because of the smaller size of the main chamber 20 the cooling and heating ramp times are much greater thereby significantly increasing the speed of trapping and thereafter vaporizing to result in more concentrated sample components and narrower and higher chromatographic spikes. The preferred speed of heating is 1200 degrees Centigrade per minute.

While particular embodiments of this invention have been shown in the drawings and described above, it will be apparent, that many changes may be made in the form, arrangement and positioning of the various elements of the combination. In consideration thereof it should be understood that preferred embodiments of this invention disclosed herein are intended to be illustrative only and not intended to limit the scope of the invention.

We claim:

1. A miniaturized cryogenic trap apparatus for selective cooling and heating of a capillary column for analyzing of volatile components passing therethrough, said miniaturized cryogenic trap apparatus including;

A. a main housing means defining a main chamber means therein for selectively cooling and heating therewithin;

B. a capillary guide tube means extending into said main housing means through said main chamber means, said capillary guide tube means defining a feedthrough bore means extending longitudinally therethrough adapted to receive the capillary column extending therethrough for selective heating and cooling of volatile components passing therethrough responsive to selective cooling and heating of said main chamber means, said feedthrough bore means extending through said main chamber means along a distance of not greater than one inch in length for miniaturization of said main chamber means;

C. a cooling fluid inlet means in fluid flow communication with respect to said main chamber means for selectively supplying cooling fluid thereinto for cooling of said feedthrough bore means extending therethrough and for cooling of volatile components passing through the capillary column positioned extending therethrough;

D. a cooling fluid outlet means in fluid flow communication with respect to said main chamber means for selectively exhausting cooling fluid therefrom in order to allow subsequent heating of said feedthrough bore means extending therethrough and for allowing heating of volatile components passing through the capillary column positioned extending therethrough; and E. a heating means at least partially positioned within said main chamber means extending about said feedthrough bore means to facilitate heating of the capillary column and of volatile components passing therethrough.

2. A miniaturized cryogenic trap apparatus for selective cooling and heating of a capillary column for analyzing of volatile components passing therethrough as defined in claim 1 wherein said main housing means defines said main chamber means in a cylindrical shape with a base diameter of less than 0.75 inches and height of less than 1.00 inches and wherein said capillary guide tube means is positioned extending axially therethrough.

3. A miniaturized cryogenic trap apparatus for selective cooling and heating of a capillary column for analyzing of volatile components passing therethrough as defined in claim 1 wherein said main chamber means is less than 0.5 cubic inches in total volume.

4. A miniaturized cryogenic trap apparatus for selective cooling and heating of a capillary column for analyzing of volatile components passing therethrough as defined in claim 1 wherein said feedthrough bore means defined in said capillary guide tube means is in abutment with the capillary column for friction engagement therewith to facilitate retaining of the capillary column extending therethrough.

5. A miniaturized cryogenic trap apparatus for selective cooling and heating of a capillary column for analyzing of volatile components passing therethrough as defined in claim 1 wherein said capillary guide tube means is of stainless steel and is fixedly secured to said main housing means to minimize leakage from said main chamber means to the surrounding environmental area.

6. A miniaturized cryogenic trap apparatus for selective cooling and heating of a capillary column for analyzing of volatile components passing therethrough as defined in claim 1 wherein said main housing means further defines an upper opening means therein and further including an upper plate means positioned extending over said upper opening means for sealing thereof against leakage through said upper opening means.

7. A miniaturized cryogenic trap apparatus for selective cooling and heating of a capillary column for analyzing of volatile components passing therethrough as defined in claim 6 wherein said main housing means includes an upper shoulder means extending peripherally around said upper opening means, said upper plate means being engageable in abutment with said upper shoulder means to facilitate retainment thereof in position extending over said upper opening means and to facilitate sealing of said main chamber means.

8. A miniaturized cryogenic trap apparatus for selective cooling and heating of a capillary column for analyzing of volatile components passing therethrough as defined in claim 6 further comprising a cap means secured to said main housing means in a position extending over said upper plate means and extending outwardly therefrom to define an upper chamber means thereadjacent, said cap means further defining a lateral opening means therein to facilitate access thereinto.

9. A miniaturized cryogenic trap apparatus for selective cooling and heating of a capillary column for analyzing of volatile components passing therethrough as defined in claim 8 wherein said heating means includes an electrical resistance heating element means extending about said capillary guide tube means within said main chamber means to facilitate selective heating of a capillary column extending therethrough.

10. A miniaturized cryogenic trap apparatus for selective cooling and heating of a capillary column for analyzing of volatile components passing therethrough as defined in claim 9 wherein said upper plate means defines a plurality of upper plate apertures therein and wherein said heating means further includes electrical lines extending through said lateral opening means of said cap means into said upper chamber means defined therein and through said upper plate apertures into said main chamber means for operative electrical connection with respect to said electrical resistance heating element.

11. A miniaturized cryogenic trap apparatus for selective cooling and heating of a capillary column for analyzing of volatile components passing therethrough as defined in claim 10 further comprising a temperature controlling means including a temperature probe means positioned within said main chamber means and a temperature monitoring line extending between said temperature probe means and said temperature controlling means, said temperature controlling means being operatively connected to said heating means for controlling operation thereof responsive to temperatures monitored within said main chamber means by said temperature probe means.

12. A miniaturized cryogenic trap apparatus for selective cooling and heating of a capillary column for analyzing of volatile components passing therethrough as defined in claim 11 wherein said temperature monitoring line extends through one of said upper plate apertures to said temperature probe means positioned within said main chamber means.

13. A miniaturized cryogenic trap apparatus for selective cooling and heating of a capillary column for analyzing of volatile components passing therethrough as defined in claim 10 further comprising a plurality of annular sealing collars each with a hole extending therethrough with one positioned within each of said upper plate apertures for abutting engagement with said electrical lines and with said temperature monitoring line passing therethrough to prevent fluid flow leakage outwardly from said main chamber means.

14. A miniaturized cryogenic trap apparatus for selective cooling and heating of a capillary column for analyzing of volatile components passing therethrough as defined in claim 13 wherein said annular sealing collars are selectively removable from said upper plate aperture to facilitate replacement thereof.

15. A miniaturized cryogenic trap apparatus for selective cooling and heating of a capillary column for analyzing of volatile components passing therethrough as defined in claim 11 wherein said temperature controlling means includes a thermocouple junction means.

16. A miniaturized cryogenic trap apparatus for selective cooling and heating of a capillary column for analyzing of volatile components passing therethrough as defined in claim 11 wherein said temperature controlling means comprises a platinum resistance thermometer.

17. A miniaturized cryogenic trap apparatus for selective cooling and heating of a capillary column for analyzing of volatile components passing therethrough as defined in claim 11 further comprising an auxiliary lateral housing means with at least a portion of said temperature controlling means fixedly secured therein to facilitate attachment of said temperature controlling means with respect to said main housing means.

18. A miniaturized cryogenic trap apparatus for selective cooling and heating of a capillary column for analyzing of volatile components passing therethrough as defined in claim 1 wherein said heating means is selectively operable to increase the temperature of the volatile components passing through the capillary column positioned extending through said capillary guide tube means at a speed of 1200 degrees Centigrade per minute.

19. For use with a gas chromatography injection port member positionable adapted to receive and guide a capillary column into an oven to facilitate analysis of volatile components passing therethrough, the improvement comprising a miniaturized cryogenic trap apparatus for selective cooling and heating of the capillary column after exiting of the injection port member, said apparatus comprising;

A. a main housing means defining a main chamber means therein for selectively cooling and heating therewithin;

B. a capillary guide tube means extending into said main housing means through said main chamber means, said capillary guide tube means defining a feedthrough bore means extending longitudinally therethrough adapted to receive the capillary column extending therethrough for selective heating and cooling of volatile components passing therethrough responsive to selective cooling and heating of said main chamber means, said feedthrough bore means extending through said main chamber means along a distance of not greater than one inch in length for miniaturization of said main chamber means;

C. a port bracket member fixedly secured to said main housing means and detachably mountable to the injection port member to facilitate positioning of the capillary column within said feedthrough bore means of said capillary guide tube means after exiting from the injection port member;

D. a cooling fluid inlet means in fluid flow communication with respect to said main chamber means for selectively supplying cooling fluid thereinto for cooling of said feedthrough bore means extending therethrough and for cooling of volatile components passing through the capillary column positioned extending therethrough;

E. a cooling fluid outlet means in fluid flow communication with respect to said main chamber means for selectively exhausting cooling fluid therefrom in order to allow subsequent heating of said feedthrough bore means extending therethrough and for allowing heating of volatile components passing through the capillary column positioned extending therethrough; and F. a heating means at least partially positioned within said main chamber means extending about said feedthrough bore means to facilitate heating of the capillary column and of volatile components passing therethrough.

20. For use with a gas chromatography injection port member positionable adapted to receive and guide a capillary column into an oven to facilitate analysis of volatile components passing therethrough, the improvement comprising a miniaturized cryogenic trap apparatus for selective cooling and heating of the capillary column after exiting of the injection port member, said apparatus comprising;

A. a main housing means defining a main chamber means therein for selectively cooling and heating therewithin, said main chamber means being cylindrically shaped including a cylindrical base diameter of less than 0.75 inches and a cylindrical height of less than 1.00 inches and wherein said capillary column is positioned extending axially therethrough, said main chamber means having a total volume of less than 0.5 cubic inches, said main housing means further defining an upper opening means therein and including an upper shoulder means extending peripherally therearound;

B. a capillary guide tube means of stainless steel extending into said main housing means axially through said cylindrically shaped main chamber means, said capillary guide tube means being fixedly attached to said main housing means to minimize leakage from said main chamber means defined therein, said capillary guide tube means defining a feedthrough bore means extending longitudinally therethrough adapted to receive a capillary column extending therethrough for selective heating and cooling of volatile components passing therethrough responsive to selective cooling and heating of said main chamber means, said feedthrough bore means extending through said main chamber means along a distance of not greater than one inch in length for miniaturization of said main chamber means, said feedthrough bore means of said capillary guide tube means being in abutting frictional engagement with the capillary column extending therethrough to facilitate retaining thereof;

C. a port bracket member fixedly secured to said main housing means and detachably mountable to the injection port member to facilitate positioning of the capillary column within said feedthrough bore means of said capillary guide tube means after exiting from the injection port member;

D. an insulation member positioned between said port bracket member and the injection port member to minimize heat flow therebetween;

E. a cooling fluid inlet means in fluid flow communication with respect to said main chamber means for selectively supplying cooling fluid thereinto for cooling of said feedthrough bore means extending therethrough and for cooling of volatile components, passing through the capillary column positioned extending therethrough;

F. a cooling fluid outlet means in fluid flow communication with respect to said main chamber means for selectively exhausting cooling fluid therefrom in order to allow subsequent heating of said feedthrough bore means extending therethrough and for allowing heating of volatile components passing through the capillary column positioned extending therethrough;

G. an upper plate means positioned in abutment with said upper shoulder means peripherally around said upper opening means and extending thereover to sealing same and preventing fluid flow leakage therefrom, said upper plate means defining a plurality of upper plate apertures therein to facilitate access therebelow into said main chamber means;

H. a cap means positioned attached to said main housing means in a position extending over said upper plate means and extending outwardly therefrom to define an upper chamber means thereabove, said cap means further defining a lateral opening means therein to facilitate access thereinto;

I. a heating means at least partially positioned within said main chamber means extending about said feedthrough bore means to facilitate heating of the capillary column and of volatile components passing therethrough, said heating means including an electrical resistance heating element means extending about said capillary guide tube means within said main chamber means to facilitate selective heating of a capillary column extending therethrough, said heating means further including electrical lines extending through said lateral opening means of said cap means into said upper chamber means defined therein and through said upper plate apertures into said main chamber means for operative electrical connection with respect to said electrical resistance heating element;

J. a temperature controlling means including a temperature probe means positioned within said main chamber means and a temperature monitoring line extending therefrom, said temperature controlling means being operative for controlling operation of said heating means responsive to temperatures monitored within said main chamber means by said temperature probe means, said temperature monitoring line extending through said lateral opening means and through one of said upper plate apertures into said main chamber means for operative connection to said temperature probe means positioned therewithin; and K. a plurality of annular sealing collars each defining a hole extending therethrough with one positioned within each of said upper plate apertures for abutting engagement with said electrical lines and with said temperature monitoring line passing there said holes to prevent fluid flow leakage outwardly from said main chamber means, said annular sealing collars being selectively removable from said upper plate apertures so to facilitate replacement thereof.

* * * * *